US008685691B2

(12) United States Patent
Sonoda et al.

(10) Patent No.: US 8,685,691 B2
(45) Date of Patent: Apr. 1, 2014

(54) METHOD FOR PRODUCING AMINOPEPTIDASE

(75) Inventors: Hiroyuki Sonoda, Hyogo (JP); Katsuya Daimon, Hyogo (JP); Atsushi Sugimura, Hyogo (JP)

(73) Assignee: JCR Pharmaceuticals Co., Ltd., Hyogo (JP)

(*) Notice: Subject to any disclaimer, the term of this patent is extended or adjusted under 35 U.S.C. 154(b) by 333 days.

(21) Appl. No.: 12/740,146

(22) PCT Filed: Oct. 25, 2008

(86) PCT No.: PCT/JP2008/069381
§ 371 (c)(1),
(2), (4) Date: Sep. 27, 2010

(87) PCT Pub. No.: WO2009/057533
PCT Pub. Date: May 7, 2009

(65) Prior Publication Data
US 2011/0027859 A1    Feb. 3, 2011

(30) Foreign Application Priority Data

Oct. 29, 2007 (JP) ................. 2007-280200

(51) Int. Cl.
*C12N 9/48* (2006.01)
*C12N 1/20* (2006.01)
*C12N 15/00* (2006.01)
*C12P 21/06* (2006.01)
*C07H 21/04* (2006.01)

(52) U.S. Cl.
USPC .... 435/212; 435/69.1; 435/252.3; 435/320.1; 536/23.2

(58) Field of Classification Search
None
See application file for complete search history.

(56) References Cited

U.S. PATENT DOCUMENTS

| 5,569,598 | A | 10/1996 | Park et al. | |
|---|---|---|---|---|
| 7,098,018 | B2 * | 8/2006 | Lee et al. | 435/222 |
| 2006/0105379 | A1 * | 5/2006 | Wu et al. | 435/6 |

FOREIGN PATENT DOCUMENTS

| JP | 62 500003 | 1/1987 |
|---|---|---|
| JP | 62 244381 | 10/1987 |
| JP | 2004 533263 | 11/2004 |
| WO | WO-86 01229 | 2/1986 |
| WO | WO-03 004635 | 1/2003 |

OTHER PUBLICATIONS

Sonoda et al. Protein Exp and Purif 62: 153-159, 2008, online publication Aug. 14, 2008.*

Victor et al. cloning, sequencing and expression of the gene encoding the extracellular neutral protease, vibriolysin, of Vibrio proteolyticus, Gene (1992), 112(1): 107-112.*
Guenet et al. Isolation of the leucine aminopeptidase gene from Aeromonas proteolytica, JBC (1992), 267(12): 8390-8395.*
Barrett, A. J. et al., "Handbook of Proteolytic Enzymes," Aspartic and Metallo Peptidase, 2004, vol. 1, pp. 399-401.
Bayliss, M. E. et al., "Aeromonas Neutral Protease: Specificity Toward Extended Substrates [1,2]," Archives of Biochemistry and Biophysics, Oct. 1, 1980, vol. 204, No. 1, pp. 214-219.
Bzymek, K. P. et al., "Function of the signal peptide and N- and C-terminal propeptides in the leucine aminopeptidase from Aeromonas proteolytica," Protein Expression and Purification , 2004, vol. 37, pp. 294-305.
Durham, D. R., "The unique stability of vibrio proteolyticus neutral protease under alkaline conditions affords a selective step for purification and use in amino acid-coupling reactions," Applied and Environmental Microbiology, Aug. 1990, pp. 2277-2281.
International Search Report for PCT/JP2008/069381 dated Jan. 6, 2009.
Lorand, L., "Methods in enzymology Volume XLV Proteolytic Enzymes Part B," Endopeptidases, 1976, vol. 33, pp. 404-415.
Marsh, J. W. et al., "Identification of the Vibrio cholerae type 4 prepilin peptidase required for cholera toxin secretion and pilus formation," Molecular Microbiology, 1998, vol. 29, No. 6, pp. 1481-1492.
Sonoda, H. et al., "Efficient production of active Vibrio proteolyticus aminopeptidase in *Escherichia coli* by co-expression with engineered vibriolysin," Appl Microbiol Biotechnol, 2009, vol. 84, pp. 191-198.
Supplementary European Search Report for EP 08 84 4506 dated Nov. 16, 2010.
Zhang, Z. et al., "Function of the N-terminal propeptide of an aminopeptidase from Vibrio proteolyticus," Biochem J. 2000, vol. 350, pp. 671-676.
KANEBO LTD., "Novel Aminopeptidase," Patent Abstracts of Japan, Publication Date: Oct. 24, 1987: English Abstract of JP-62 244381.
Durham, D. R. et al., "The unique stability of vibrio proteolyticus neutral protease under alkaline conditions affords a selective step for purification and use in amino acid-coupling reactions," Applied and Environmental Microbiology, Aug. 1990, vol. 56, No. 8, pp. 2277-2281.
Nirasawa, S. et al., "Molecular cloning and expression in *Escherichia coli* of the extracellular endoprotease of Aeromonas caviae T-64, a pro-aminopeptidase processing enzyme," Biochimica et Biophysica Acta, 1999, vol. 1433, pp. 335-342.
Zhang, Z. et al., "Function of the N-terminal propeptide of an aminopeptidase from vibrio proteolyticus," Biochem. J., 2000, vol. 350, pp. 671-676.

* cited by examiner

*Primary Examiner* — Iqbal H Chowdhury
(74) *Attorney, Agent, or Firm* — Millen, White, Zelano & Branigan, P.C.

(57) ABSTRACT

Disclosed is an efficient method for production of aminopeptidase. The method comprises either transforming host bacteria with an aminopeptidase gene and with a neutral protease gene, or transforming some part of host bacteria with an aminopeptidase gene while transforming the other part of the host bacteria with a neutral protease gene, culturing in a medium the hose bacteria transformed with the aminopeptidase gene and with the neutral protease gene, or culturing a mixture of the host bacteria transformed with the aminopeptidase gene and the host bacteria transformed with the neutral protease gene, to let both the aminopeptidase and the neutral protease be expressed, and collecting the aminopeptidase thus produced from the culture mixture.

8 Claims, 5 Drawing Sheets

(A) pRL-AP (B) pET-AP (C) pCDF-nprV (A) pRL-AP (B) pET-AP (C) pCDF-nprV

SEQUENCE LISTING

<160> NUMBER OF SEQ ID NOS: 18

<210> SEQ ID NO 1
<211> LENGTH: 41
<212> TYPE: DNA
<213> ORGANISM: Artificial
<220> FEATURE:
<223> OTHER INFORMATION: Primer BaRBFL41

<400> SEQUENCE: 1
cgggatccta aggaggttat catatgaaat ataccaaaac g         41

<210> SEQ ID NO 2
<211> LENGTH: 33
<212> TYPE: DNA
<213> ORGANISM: Artificial
<220> FEATURE:
<223> OTHER INFORMATION: Primer No-FL33R

<400> SEQUENCE: 2
cggcggccgc ttatcagaaa gtgctggctt tca         33

```
<210> SEQ ID NO 3
<211> LENGTH: 1515
<212> TYPE: DNA
<213> ORGANISM: Vibrio proteolyticus
<220> FEATURE:
<221> NAME/KEY: CDS
<222> LOCATION: (1)..(1515)
<223> OTHER INFORMATION:

<400> SEQUENCE: 3 atg aaa tat acc aaa acg tta ctg gct atg gtt ctt tcc gcc act ttt      48
Met Lys Tyr Thr Lys Thr Leu Leu Ala Met Val Leu Ser Ala Thr Phe
1               5                   10                  15 tgt cag gct tac gcc gaa gac aaa gtg tgg atc tca att ggt gcg gac      96
Cys Gln Ala Tyr Ala Glu Asp Lys Val Trp Ile Ser Ile Gly Ala Asp
            20                  25                  30 gcc aat caa acg gtg atg aag tcc ggg gca gaa tcc att ctt ccg aat     144
Ala Asn Gln Thr Val Met Lys Ser Gly Ala Glu Ser Ile Leu Pro Asn
        35                  40                  45 tcc gtc gcc agc agt ggt cag gtg tgg gtt gga caa gtc gat gtc gct     192
Ser Val Ala Ser Ser Gly Gln Val Trp Val Gly Gln Val Asp Val Ala
    50                  55                  60 cag ctc gct gag ctt tcg cat aat atg cac gaa gag cat aat cgc tgt     240
Gln Leu Ala Glu Leu Ser His Asn Met His Glu Glu His Asn Arg Cys
65                  70                  75                  80 ggt ggg tac atg gta cac cct tca gcg caa agt gcg atg gcg gca agt     288
Gly Gly Tyr Met Val His Pro Ser Ala Gln Ser Ala Met Ala Ala Ser
                85                  90                  95 gcg atg ccc act acg cta gcc agc ttc gtg atg ccg ccg att aca cag     336
Ala Met Pro Thr Thr Leu Ala Ser Phe Val Met Pro Pro Ile Thr Gln
            100                 105                 110 cag gcg acc gtc aca gcg tgg ctg cct cag gtt gac gcg tca caa atc     384
Gln Ala Thr Val Thr Ala Trp Leu Pro Gln Val Asp Ala Ser Gln Ile
        115                 120                 125 acc ggg acc atc agt tcg ctg gag agc ttc acc aac cgt ttt tac acc     432
Thr Gly Thr Ile Ser Ser Leu Glu Ser Phe Thr Asn Arg Phe Tyr Thr
    130                 135                 140 acc act tct gga gct cag gcc tcg gac tgg ata gcc agc gaa tgg cag     480
Thr Thr Ser Gly Ala Gln Ala Ser Asp Trp Ile Ala Ser Glu Trp Gln
145                 150                 155                 160 gct ctg tca gcc tct ctg ccc aat gcc agc gtc aag caa gtg tct cac     528
Ala Leu Ser Ala Ser Leu Pro Asn Ala Ser Val Lys Gln Val Ser His
                165                 170                 175 tca ggc tac aac caa aag tcg gtc gtt atg acc att aca ggc tca gaa     576
Ser Gly Tyr Asn Gln Lys Ser Val Val Met Thr Ile Thr Gly Ser Glu
            180                 185                 190 gcg cct gac gag tgg att gtg att ggt ggt cac ctt gat tcg acc att     624
Ala Pro Asp Glu Trp Ile Val Ile Gly Gly His Leu Asp Ser Thr Ile
        195                 200                 205 ggt tca cac acc aac gaa caa agt gtt gca ccg ggt gcg gat gat gat     672
Gly Ser His Thr Asn Glu Gln Ser Val Ala Pro Gly Ala Asp Asp Asp
    210                 215                 220 gct tcg ggt atc gca gcc gtc act gaa gtg atc cgt gtg ctg tca gag     720
Ala Ser Gly Ile Ala Ala Val Thr Glu Val Ile Arg Val Leu Ser Glu
225                 230                 235                 240 aac aac ttc caa cca aaa cgt agc att gcc ttc atg gct tat gcc gct     768
Asn Asn Phe Gln Pro Lys Arg Ser Ile Ala Phe Met Ala Tyr Ala Ala
                245                 250                 255 gag gaa gtc ggc ttg cgt ggt tca caa gat ctg gcg aat cag tat aaa     816
Glu Glu Val Gly Leu Arg Gly Ser Gln Asp Leu Ala Asn Gln Tyr Lys
            260                 265                 270
```

```
tcc gaa ggt aaa aac gtg gtt tcc gcc ctg caa ctg gac atg acc aac     864
Ser Glu Gly Lys Asn Val Val Ser Ala Leu Gln Leu Asp Met Thr Asn
        275                 280                 285 tac aaa ggt tct gcc caa gat gtc gtg ttt atc acc gat tac act gac     912
Tyr Lys Gly Ser Ala Gln Asp Val Val Phe Ile Thr Asp Tyr Thr Asp
    290                 295                 300 agc aac ttc act caa tat ctg acg cag cta atg gac gag tat ttg ccg     960
Ser Asn Phe Thr Gln Tyr Leu Thr Gln Leu Met Asp Glu Tyr Leu Pro
305                 310                 315                 320 agt ctg act tac ggt ttc gat act tgc ggg tac gcc tgt tct gat cac    1008
Ser Leu Thr Tyr Gly Phe Asp Thr Cys Gly Tyr Ala Cys Ser Asp His
                325                 330                 335 gca tca tgg cac aac gct ggc tac ccc gcc gcc atg ccg ttt gag tcg    1056
Ala Ser Trp His Asn Ala Gly Tyr Pro Ala Ala Met Pro Phe Glu Ser
            340                 345                 350 aag ttc aac gat tac aat ccg cgt att cac acc act caa gat acg ttg    1104
Lys Phe Asn Asp Tyr Asn Pro Arg Ile His Thr Thr Gln Asp Thr Leu
        355                 360                 365 gcg aac tcc gat cca acc ggc tct cat gcc aag aag ttc act cag tta    1152
Ala Asn Ser Asp Pro Thr Gly Ser His Ala Lys Lys Phe Thr Gln Leu
    370                 375                 380 ggt ctt gct tat gcg att gaa atg ggc agc gca acc ggt gac aca cca    1200
Gly Leu Ala Tyr Ala Ile Glu Met Gly Ser Ala Thr Gly Asp Thr Pro
385                 390                 395                 400 aca cca ggc aat cag ctg gaa gac ggt gtg cct gtc acc gat ttg tct    1248
Thr Pro Gly Asn Gln Leu Glu Asp Gly Val Pro Val Thr Asp Leu Ser
                405                 410                 415 ggt agc cga ggc agc aac gta tgg tat acg ttt gaa ctg gaa acc cag    1296
Gly Ser Arg Gly Ser Asn Val Trp Tyr Thr Phe Glu Leu Glu Thr Gln
            420                 425                 430 aaa aac ctg caa atc acc acc tct ggt ggc tat ggt gat ctg gac ttg    1344
Lys Asn Leu Gln Ile Thr Thr Ser Gly Gly Tyr Gly Asp Leu Asp Leu
        435                 440                 445 tat gtg aag ttt ggc agt aaa gcc agc aaa cag aac tgg gat tgc cgc    1392
Tyr Val Lys Phe Gly Ser Lys Ala Ser Lys Gln Asn Trp Asp Cys Arg
    450                 455                 460 cca tat ctc agt ggg aac aac gaa gtc tgt acg ttc aac aat gct tca    1440
Pro Tyr Leu Ser Gly Asn Asn Glu Val Cys Thr Phe Asn Asn Ala Ser
465                 470                 475                 480 cca ggc acc tac tcc gtc atg ctg aca ggg tac tcc aac tac agc gga    1488
Pro Gly Thr Tyr Ser Val Met Leu Thr Gly Tyr Ser Asn Tyr Ser Gly
                485                 490                 495 gcc agc ctg aaa gcc agc act ttc tga                                1515
Ala Ser Leu Lys Ala Ser Thr Phe
            500

<210> SEQ ID NO 4
<211> LENGTH: 504
<212> TYPE: PRT
<213> ORGANISM: Vibrio proteolyticus

<400> SEQUENCE: 4

Met Lys Tyr Thr Lys Thr Leu Leu Ala Met Val Leu Ser Ala Thr Phe
1               5                   10                  15

Cys Gln Ala Tyr Ala Glu Asp Lys Val Trp Ile Ser Ile Gly Ala Asp
            20                  25                  30

Ala Asn Gln Thr Val Met Lys Ser Gly Ala Glu Ser Ile Leu Pro Asn
        35                  40                  45

Ser Val Ala Ser Ser Gly Gln Val Trp Val Gly Gln Val Asp Val Ala
    50                  55                  60
```

```
Gln Leu Ala Glu Leu Ser His Asn Met His Glu Glu His Asn Arg Cys
65                  70                  75                  80

Gly Gly Tyr Met Val His Pro Ser Ala Gln Ser Ala Met Ala Ala Ser
                85                  90                  95

Ala Met Pro Thr Thr Leu Ala Ser Phe Val Met Pro Pro Ile Thr Gln
            100                 105                 110

Gln Ala Thr Val Thr Ala Trp Leu Pro Gln Val Asp Ala Ser Gln Ile
        115                 120                 125

Thr Gly Thr Ile Ser Ser Leu Glu Ser Phe Thr Asn Arg Phe Tyr Thr
    130                 135                 140

Thr Thr Ser Gly Ala Gln Ala Ser Asp Trp Ile Ala Ser Glu Trp Gln
145                 150                 155                 160

Ala Leu Ser Ala Ser Leu Pro Asn Ala Ser Val Lys Gln Val Ser His
                165                 170                 175

Ser Gly Tyr Asn Gln Lys Ser Val Val Met Thr Ile Thr Gly Ser Glu
            180                 185                 190

Ala Pro Asp Glu Trp Ile Val Ile Gly Gly His Leu Asp Ser Thr Ile
        195                 200                 205

Gly Ser His Thr Asn Glu Gln Ser Val Ala Pro Gly Ala Asp Asp Asp
    210                 215                 220

Ala Ser Gly Ile Ala Ala Val Thr Glu Val Ile Arg Val Leu Ser Glu
225                 230                 235                 240

Asn Asn Phe Gln Pro Lys Arg Ser Ile Ala Phe Met Ala Tyr Ala Ala
                245                 250                 255

Glu Glu Val Gly Leu Arg Gly Ser Gln Asp Leu Ala Asn Gln Tyr Lys
            260                 265                 270

Ser Glu Gly Lys Asn Val Val Ser Ala Leu Gln Leu Asp Met Thr Asn
        275                 280                 285

Tyr Lys Gly Ser Ala Gln Asp Val Val Phe Ile Thr Asp Tyr Thr Asp
    290                 295                 300

Ser Asn Phe Thr Gln Tyr Leu Thr Gln Leu Met Asp Glu Tyr Leu Pro
305                 310                 315                 320

Ser Leu Thr Tyr Gly Phe Asp Thr Cys Gly Tyr Ala Cys Ser Asp His
                325                 330                 335

Ala Ser Trp His Asn Ala Gly Tyr Pro Ala Ala Met Pro Phe Glu Ser
            340                 345                 350

Lys Phe Asn Asp Tyr Asn Pro Arg Ile His Thr Thr Gln Asp Thr Leu
        355                 360                 365

Ala Asn Ser Asp Pro Thr Gly Ser His Ala Lys Lys Phe Thr Gln Leu
    370                 375                 380

Gly Leu Ala Tyr Ala Ile Glu Met Gly Ser Ala Thr Gly Asp Thr Pro
385                 390                 395                 400

Thr Pro Gly Asn Gln Leu Glu Asp Gly Val Pro Val Thr Asp Leu Ser
                405                 410                 415

Gly Ser Arg Gly Ser Asn Val Trp Tyr Thr Phe Glu Leu Glu Thr Gln
            420                 425                 430

Lys Asn Leu Gln Ile Thr Thr Ser Gly Tyr Gly Asp Leu Asp Leu
        435                 440                 445

Tyr Val Lys Phe Gly Ser Lys Ala Ser Lys Gln Asn Trp Asp Cys Arg
    450                 455                 460

Pro Tyr Leu Ser Gly Asn Asn Glu Val Cys Thr Phe Asn Asn Ala Ser
465                 470                 475                 480

Pro Gly Thr Tyr Ser Val Met Leu Thr Gly Tyr Ser Asn Tyr Ser Gly
                485                 490                 495
```

Ala Ser Leu Lys Ala Ser Thr Phe
            500

<210> SEQ ID NO 5
<211> LENGTH: 44
<212> TYPE: DNA
<213> ORGANISM: Artificial
<220> FEATURE:
<223> OTHER INFORMATION: Primer PelB-1F

<400> SEQUENCE: 5
acgggatcct aaggaggtta tcatatgaaa tacctgctgc ccac            44

<210> SEQ ID NO 6
<211> LENGTH: 45
<212> TYPE: DNA
<213> ORGANISM: Artificial
<220> FEATURE:
<223> OTHER INFORMATION: Primer PelB-2R

<400> SEQUENCE: 6
caggagcagc agaccagcag cagcggtggg cagcaggtat ttcat           45

<210> SEQ ID NO 7
<211> LENGTH: 43
<212> TYPE: DNA
<213> ORGANISM: Artificial
<220> FEATURE:
<223> OTHER INFORMATION: Primer PelB-3F

<400> SEQUENCE: 7
gctggtctgc tgctcctggc tgcccaaccc gcgatggccg aag             43

<210> SEQ ID NO 8
<211> LENGTH: 44
<212> TYPE: DNA
<213> ORGANISM: Artificial
<220> FEATURE:
<223> OTHER INFORMATION: Primer PelB-4R

<400> SEQUENCE: 8
cgcaccaatt gagatccaca ctttgtcttc ggccatcgcg ggtt            44

<210> SEQ ID NO 9
<211> LENGTH: 63
<212> TYPE: DNA
<213> ORGANISM: Vibrio proteolyticus

<400> SEQUENCE: 9
atgaaatata ccaaaacgtt actggctatg gttctttccg ccactttttg tcaggcttac    60
gcc                                                                 63

<210> SEQ ID NO 10
<211> LENGTH: 66
<212> TYPE: DNA
<213> ORGANISM: Artificial
<220> FEATURE:
<223> OTHER INFORMATION: Synthetic PelB

<400> SEQUENCE: 10
atgaaatacc tgctgcccac cgctgctgct ggtctgctgc tcctggctgc ccaacccgcg    60
atggcc                                                              66

<210> SEQ ID NO 11

<211> LENGTH: 1830
<212> TYPE: DNA
<213> ORGANISM: Vibrio proteolyticus
<220> FEATURE:
<221> NAME/KEY: CDS
<222> LOCATION: (1)..(1830)
<223> OTHER INFORMATION:

<400> SEQUENCE: 11

```
atg aat aaa aca caa cgt cac atc aac tgg ctg ctg gct gtt agc gcg      48
Met Asn Lys Thr Gln Arg His Ile Asn Trp Leu Leu Ala Val Ser Ala
1               5                   10                  15 gca act gcg cta cct gtc acc gct gca gaa atg atc aac gta aat gat      96
Ala Thr Ala Leu Pro Val Thr Ala Ala Glu Met Ile Asn Val Asn Asp
            20                  25                  30 ggc agc ctg cta aac cag gct ctt aaa gct cag tca cag agc gtt gcc     144
Gly Ser Leu Leu Asn Gln Ala Leu Lys Ala Gln Ser Gln Ser Val Ala
        35                  40                  45 ccg gtg gaa acc gga ttc aaa caa atg aaa cga gtt gtt ttg cca aat     192
Pro Val Glu Thr Gly Phe Lys Gln Met Lys Arg Val Val Leu Pro Asn
    50                  55                  60 ggc aaa gtg aaa gtt cgt tat caa caa act cac cac ggt cta ccg gtt     240
Gly Lys Val Lys Val Arg Tyr Gln Gln Thr His His Gly Leu Pro Val
65                  70                  75                  80 ttc aac acc tcg gta gtg gcg act gaa tcg aag tct ggt agt agc gaa     288
Phe Asn Thr Ser Val Val Ala Thr Glu Ser Lys Ser Gly Ser Ser Glu
                85                  90                  95 gtg ttc ggt gtg atg gct cag ggt atc gca gac gac gtg tct aca ctg     336
Val Phe Gly Val Met Ala Gln Gly Ile Ala Asp Asp Val Ser Thr Leu
            100                 105                 110 acg cca tcc gtt gag atg aag cag gcc att tca att gct aaa tcg cgt     384
Thr Pro Ser Val Glu Met Lys Gln Ala Ile Ser Ile Ala Lys Ser Arg
        115                 120                 125 ttc caa cag caa gaa aaa atg gtt gcg gaa cct gca acg gaa aac gaa     432
Phe Gln Gln Gln Glu Lys Met Val Ala Glu Pro Ala Thr Glu Asn Glu
    130                 135                 140 aaa gcc gag ttg atg gtt cgt ctg gac gac aac aat caa gcg caa cta     480
Lys Ala Glu Leu Met Val Arg Leu Asp Asp Asn Asn Gln Ala Gln Leu
145                 150                 155                 160 gtg tat ctg gtt gat ttc ttc gtt gcc gag gat cac cca gcg cgt cct     528
Val Tyr Leu Val Asp Phe Phe Val Ala Glu Asp His Pro Ala Arg Pro
                165                 170                 175 ttc ttt ttc att gat gcg caa acg ggt gaa gta ctg caa act tgg gat     576
Phe Phe Phe Ile Asp Ala Gln Thr Gly Glu Val Leu Gln Thr Trp Asp
            180                 185                 190 ggt ctg aac cat gca caa gct gac ggt act ggc cct ggc ggt aac acc     624
Gly Leu Asn His Ala Gln Ala Asp Gly Thr Gly Pro Gly Gly Asn Thr
        195                 200                 205 aaa aca ggt cgt tat gaa tac ggt tct gac ttt cct ccg ttt gtc atc     672
Lys Thr Gly Arg Tyr Glu Tyr Gly Ser Asp Phe Pro Pro Phe Val Ile
    210                 215                 220 gat aaa gtc ggc act aag tgt tca atg aac aac agc gcg gta aga acg     720
Asp Lys Val Gly Thr Lys Cys Ser Met Asn Asn Ser Ala Val Arg Thr
225                 230                 235                 240 gtt gac ctg aac ggc tca act tca ggt aac acc act tac agc tat acc     768
Val Asp Leu Asn Gly Ser Thr Ser Gly Asn Thr Thr Tyr Ser Tyr Thr
                245                 250                 255 tgt aac gac tca acc aac tac aac gat tac aaa gcc att aac ggc gcg     816
Cys Asn Asp Ser Thr Asn Tyr Asn Asp Tyr Lys Ala Ile Asn Gly Ala
            260                 265                 270 tac tcg cca ctg aac gat gcc cac tac ttc ggt aaa gtg gtt ttc gat     864
Tyr Ser Pro Leu Asn Asp Ala His Tyr Phe Gly Lys Val Val Phe Asp
```

```
              275                 280                 285
atg tac aaa gac tgg atg aac acc aca cca ctg acg ttc cag ctg act       912
Met Tyr Lys Asp Trp Met Asn Thr Thr Pro Leu Thr Phe Gln Leu Thr
    290                 295                 300 atg cgt gtt cac tat ggt aac aac tac gaa aac gcg ttc tgg aat ggt       960
Met Arg Val His Tyr Gly Asn Asn Tyr Glu Asn Ala Phe Trp Asn Gly
305                 310                 315                 320 tca tcc atg acc ttc ggt gat ggc tac agc acc ttc tac ccg ctg gtg      1008
Ser Ser Met Thr Phe Gly Asp Gly Tyr Ser Thr Phe Tyr Pro Leu Val
                325                 330                 335 gat att aac gtt agt gcc cac gaa gtg agc cac ggt ttc acc gaa caa      1056
Asp Ile Asn Val Ser Ala His Glu Val Ser His Gly Phe Thr Glu Gln
        340                 345                 350 aac tcg ggt ctg gtg tac gag aat atg tct ggt ggt atg aac gaa gcg      1104
Asn Ser Gly Leu Val Tyr Glu Asn Met Ser Gly Gly Met Asn Glu Ala
    355                 360                 365 ttc tct gat att gca ggt gaa gca gca gag ttc tac atg aaa ggc agc      1152
Phe Ser Asp Ile Ala Gly Glu Ala Ala Glu Phe Tyr Met Lys Gly Ser
370                 375                 380 gtt gac tgg gtt gtc ggt gcg gat atc ttc aaa tca tcc ggc ggt ctg      1200
Val Asp Trp Val Val Gly Ala Asp Ile Phe Lys Ser Ser Gly Gly Leu
385                 390                 395                 400 cgt tac ttt gat cag cct tcg cgt gac ggc cgt tct atc gac cat gcg      1248
Arg Tyr Phe Asp Gln Pro Ser Arg Asp Gly Arg Ser Ile Asp His Ala
                405                 410                 415 tct gac tac tac aat ggc ctg aat gtt cac tac tca agt ggt gta ttc      1296
Ser Asp Tyr Tyr Asn Gly Leu Asn Val His Tyr Ser Ser Gly Val Phe
        420                 425                 430 aac cgt gcg ttc tac ctg ctg gct aac aaa gcg ggt tgg gat gta cgc      1344
Asn Arg Ala Phe Tyr Leu Leu Ala Asn Lys Ala Gly Trp Asp Val Arg
    435                 440                 445 aaa ggc ttt gaa gtg ttt acc ctg gct aac caa ttg tac tgg aca gcg      1392
Lys Gly Phe Glu Val Phe Thr Leu Ala Asn Gln Leu Tyr Trp Thr Ala
450                 455                 460 aac agc aca ttt gat gaa ggc ggt tgt ggt gta gtg aaa gct gcg agc      1440
Asn Ser Thr Phe Asp Glu Gly Gly Cys Gly Val Val Lys Ala Ala Ser
465                 470                 475                 480 gac atg ggt tac agc gtt gca gac gta gaa gat gcg ttt aac acg gta      1488
Asp Met Gly Tyr Ser Val Ala Asp Val Glu Asp Ala Phe Asn Thr Val
                485                 490                 495 ggc gtt aac gcg tct tgt ggt gca act cct cct ccg tct ggc gat gta      1536
Gly Val Asn Ala Ser Cys Gly Ala Thr Pro Pro Pro Ser Gly Asp Val
        500                 505                 510 ctg gaa atc ggt aaa ccg ctg gcg aac ctt tca ggt aac cgc aat gac      1584
Leu Glu Ile Gly Lys Pro Leu Ala Asn Leu Ser Gly Asn Arg Asn Asp
    515                 520                 525 atg act tac tac acg ttc aca cca agc agc tca tct agc gta gtg att      1632
Met Thr Tyr Tyr Thr Phe Thr Pro Ser Ser Ser Ser Ser Val Val Ile
530                 535                 540 aag atc act ggc ggt aca ggt gat gca gac ctt tac gtg aaa gcg ggt      1680
Lys Ile Thr Gly Gly Thr Gly Asp Ala Asp Leu Tyr Val Lys Ala Gly
545                 550                 555                 560 agc aag cca acc acg act tct tac gat tgc cgt cca tat aag tat ggt      1728
Ser Lys Pro Thr Thr Thr Ser Tyr Asp Cys Arg Pro Tyr Lys Tyr Gly
                565                 570                 575 aac gaa gag cag tgt tca att tca gcg caa gcg ggt act acg tat cac      1776
Asn Glu Glu Gln Cys Ser Ile Ser Ala Gln Ala Gly Thr Thr Tyr His
        580                 585                 590 gtt atg ctg cgt ggt tac agc aat tac gct ggt gta act ttg cgt gct      1824
Val Met Leu Arg Gly Tyr Ser Asn Tyr Ala Gly Val Thr Leu Arg Ala
```

-continued

```
                595                 600                 605
gac taa                                                                        1830
Asp <210> SEQ ID NO 12
<211> LENGTH: 609
<212> TYPE: PRT
<213> ORGANISM: Vibrio proteolyticus

<400> SEQUENCE: 12

Met Asn Lys Thr Gln Arg His Ile Asn Trp Leu Leu Ala Val Ser Ala
1               5                   10                  15

Ala Thr Ala Leu Pro Val Thr Ala Ala Glu Met Ile Asn Val Asn Asp
            20                  25                  30

Gly Ser Leu Leu Asn Gln Ala Leu Lys Ala Gln Ser Gln Ser Val Ala
        35                  40                  45

Pro Val Glu Thr Gly Phe Lys Gln Met Lys Arg Val Val Leu Pro Asn
    50                  55                  60

Gly Lys Val Lys Val Arg Tyr Gln Gln Thr His His Gly Leu Pro Val
65                  70                  75                  80

Phe Asn Thr Ser Val Ala Thr Glu Ser Lys Ser Gly Ser Ser Glu
                85                  90                  95

Val Phe Gly Val Met Ala Gln Gly Ile Ala Asp Asp Val Ser Thr Leu
            100                 105                 110

Thr Pro Ser Val Glu Met Lys Gln Ala Ile Ser Ile Ala Lys Ser Arg
        115                 120                 125

Phe Gln Gln Gln Glu Lys Met Val Ala Glu Pro Ala Thr Glu Asn Glu
    130                 135                 140

Lys Ala Glu Leu Met Val Arg Leu Asp Asp Asn Gln Ala Gln Leu
145                 150                 155                 160

Val Tyr Leu Val Asp Phe Phe Val Ala Glu Asp His Pro Ala Arg Pro
                165                 170                 175

Phe Phe Phe Ile Asp Ala Gln Thr Gly Glu Val Leu Gln Thr Trp Asp
            180                 185                 190

Gly Leu Asn His Ala Gln Ala Asp Gly Thr Gly Pro Gly Asn Thr
        195                 200                 205

Lys Thr Gly Arg Tyr Glu Tyr Gly Ser Asp Phe Pro Pro Phe Val Ile
    210                 215                 220

Asp Lys Val Gly Thr Lys Cys Ser Met Asn Asn Ser Ala Val Arg Thr
225                 230                 235                 240

Val Asp Leu Asn Gly Ser Thr Ser Gly Asn Thr Thr Tyr Ser Tyr Thr
                245                 250                 255

Cys Asn Asp Ser Thr Asn Tyr Asn Asp Tyr Lys Ala Ile Asn Gly Ala
            260                 265                 270

Tyr Ser Pro Leu Asn Asp Ala His Tyr Phe Gly Lys Val Val Phe Asp
        275                 280                 285

Met Tyr Lys Asp Trp Met Asn Thr Thr Pro Leu Thr Phe Gln Leu Thr
    290                 295                 300

Met Arg Val His Tyr Gly Asn Asn Tyr Glu Asn Ala Phe Trp Asn Gly
305                 310                 315                 320

Ser Ser Met Thr Phe Gly Asp Gly Tyr Ser Thr Phe Tyr Pro Leu Val
                325                 330                 335

Asp Ile Asn Val Ser Ala His Glu Val Ser His Gly Phe Thr Glu Gln
            340                 345                 350

Asn Ser Gly Leu Val Tyr Glu Asn Met Ser Gly Gly Met Asn Glu Ala
```

```
                355                 360                 365
Phe Ser Asp Ile Ala Gly Glu Ala Ala Glu Phe Tyr Met Lys Gly Ser
370                 375                 380

Val Asp Trp Val Val Gly Ala Asp Ile Phe Lys Ser Ser Gly Gly Leu
385                 390                 395                 400

Arg Tyr Phe Asp Gln Pro Ser Arg Asp Gly Arg Ser Ile Asp His Ala
                405                 410                 415

Ser Asp Tyr Tyr Asn Gly Leu Asn Val His Tyr Ser Ser Gly Val Phe
                420                 425                 430

Asn Arg Ala Phe Tyr Leu Leu Ala Asn Lys Ala Gly Trp Asp Val Arg
            435                 440                 445

Lys Gly Phe Glu Val Phe Thr Leu Ala Asn Gln Leu Tyr Trp Thr Ala
450                 455                 460

Asn Ser Thr Phe Asp Glu Gly Gly Cys Gly Val Val Lys Ala Ala Ser
465                 470                 475                 480

Asp Met Gly Tyr Ser Val Ala Asp Val Glu Asp Ala Phe Asn Thr Val
                485                 490                 495

Gly Val Asn Ala Ser Cys Gly Ala Thr Pro Pro Ser Gly Asp Val
                500                 505                 510

Leu Glu Ile Gly Lys Pro Leu Ala Asn Leu Ser Gly Asn Arg Asn Asp
            515                 520                 525

Met Thr Tyr Tyr Thr Phe Thr Pro Ser Ser Ser Ser Val Val Ile
530                 535                 540

Lys Ile Thr Gly Gly Thr Gly Asp Ala Asp Leu Tyr Val Lys Ala Gly
545                 550                 555                 560

Ser Lys Pro Thr Thr Thr Ser Tyr Asp Cys Arg Pro Tyr Lys Tyr Gly
                565                 570                 575

Asn Glu Glu Gln Cys Ser Ile Ser Ala Gln Ala Gly Thr Thr Tyr His
            580                 585                 590

Val Met Leu Arg Gly Tyr Ser Asn Tyr Ala Gly Val Thr Leu Arg Ala
        595                 600                 605

Asp

<210> SEQ ID NO 13
<211> LENGTH: 44
<212> TYPE: DNA
<213> ORGANISM: Artificial
<220> FEATURE:
<223> OTHER INFORMATION: Primer nprV_NcoI_FW

<400> SEQUENCE: 13
gcataatcca tggcaaaata aaacacaacg tcacatcaac tggc                        44

<210> SEQ ID NO 14
<211> LENGTH: 46
<212> TYPE: DNA
<213> ORGANISM: Artificial
<220> FEATURE:
<223> OTHER INFORMATION: Primer nprV_NotI_BamHI_RV

<400> SEQUENCE: 14
gcataatgcg gccgcggatc cattagtcag cacgcaaagt tacacc                      46

<210> SEQ ID NO 15
<211> LENGTH: 516
<212> TYPE: DNA
<213> ORGANISM: Vibrio proteolyticus
<220> FEATURE:
<221> NAME/KEY: CDS
```

<222> LOCATION: (1)..(516)
<223> OTHER INFORMATION:

<400> SEQUENCE: 15

```
gca gaa atg atc aac gta aat gat ggc agc ctg cta aac cag gct ctt    48
Ala Glu Met Ile Asn Val Asn Asp Gly Ser Leu Leu Asn Gln Ala Leu
1               5                   10                  15 aaa gct cag tca cag agc gtt gcc ccg gtg gaa acc gga ttc aaa caa    96
Lys Ala Gln Ser Gln Ser Val Ala Pro Val Glu Thr Gly Phe Lys Gln
                20                  25                  30 atg aaa cga gtt gtt ttg cca aat ggc aaa gtg aaa gtt cgt tat caa   144
Met Lys Arg Val Val Leu Pro Asn Gly Lys Val Lys Val Arg Tyr Gln
            35                  40                  45 caa act cac cac ggt cta ccg gtt ttc aac acc tcg gta gtg gcg act   192
Gln Thr His His Gly Leu Pro Val Phe Asn Thr Ser Val Val Ala Thr
        50                  55                  60 gaa tcg aag tct ggt agt agc gaa gtg ttc ggt gtg atg gct cag ggt   240
Glu Ser Lys Ser Gly Ser Ser Glu Val Phe Gly Val Met Ala Gln Gly
65                  70                  75                  80 atc gca gac gac gtg tct aca ctg acg cca tcc gtt gag atg aag cag   288
Ile Ala Asp Asp Val Ser Thr Leu Thr Pro Ser Val Glu Met Lys Gln
                85                  90                  95 gcc att tca att gct aaa tcg cgt ttc caa cag caa gaa aaa atg gtt   336
Ala Ile Ser Ile Ala Lys Ser Arg Phe Gln Gln Gln Glu Lys Met Val
                100                 105                 110 gcg gaa cct gca acg gaa aac gaa aaa gcc gag ttg atg gtt cgt ctg   384
Ala Glu Pro Ala Thr Glu Asn Glu Lys Ala Glu Leu Met Val Arg Leu
            115                 120                 125 gac gac aac aat caa gcg caa cta gtg tat ctg gtt gat ttc ttc gtt   432
Asp Asp Asn Asn Gln Ala Gln Leu Val Tyr Leu Val Asp Phe Phe Val
        130                 135                 140 gcc gag gat cac cca gcg cgt cct ttc ttt ttc att gat gtg caa acg   480
Ala Glu Asp His Pro Ala Arg Pro Phe Phe Phe Ile Asp Val Gln Thr
145                 150                 155                 160 ggt gaa gta ctg caa act tgg gat ggt ctg aac cat                   516
Gly Glu Val Leu Gln Thr Trp Asp Gly Leu Asn His
                165                 170
```

<210> SEQ ID NO 16
<211> LENGTH: 172
<212> TYPE: PRT
<213> ORGANISM: Vibrio proteolyticus

<400> SEQUENCE: 16

```
Ala Glu Met Ile Asn Val Asn Asp Gly Ser Leu Leu Asn Gln Ala Leu
1               5                   10                  15

Lys Ala Gln Ser Gln Ser Val Ala Pro Val Glu Thr Gly Phe Lys Gln
                20                  25                  30

Met Lys Arg Val Val Leu Pro Asn Gly Lys Val Lys Val Arg Tyr Gln
            35                  40                  45

Gln Thr His His Gly Leu Pro Val Phe Asn Thr Ser Val Val Ala Thr
        50                  55                  60

Glu Ser Lys Ser Gly Ser Ser Glu Val Phe Gly Val Met Ala Gln Gly
65                  70                  75                  80

Ile Ala Asp Asp Val Ser Thr Leu Thr Pro Ser Val Glu Met Lys Gln
                85                  90                  95

Ala Ile Ser Ile Ala Lys Ser Arg Phe Gln Gln Gln Glu Lys Met Val
                100                 105                 110

Ala Glu Pro Ala Thr Glu Asn Glu Lys Ala Glu Leu Met Val Arg Leu
            115                 120                 125
```

```
Asp Asp Asn Asn Gln Ala Gln Leu Val Tyr Leu Val Asp Phe Phe Val
    130                 135                 140

Ala Glu Asp His Pro Ala Arg Pro Phe Phe Ile Asp Val Gln Thr
145                 150                 155                 160

Gly Glu Val Leu Gln Thr Trp Asp Gly Leu Asn His
            165                 170

<210> SEQ ID NO 17
<211> LENGTH: 1242
<212> TYPE: DNA
<213> ORGANISM: Vibrio proteolyticus
<220> FEATURE:
<221> NAME/KEY: CDS
<222> LOCATION: (1)..(1242)
<223> OTHER INFORMATION:

<400> SEQUENCE: 17
```

| | | | | | | | | | | | | | | | | |
|---|---|---|---|---|---|---|---|---|---|---|---|---|---|---|---|---|
| gca caa gct gac ggt act ggc cct ggc ggt aac acc aaa aca ggt cgt | | | | | | | | | | | | | | | | 48 |
| Ala Gln Ala Asp Gly Thr Gly Pro Gly Gly Asn Thr Lys Thr Gly Arg | | | | | | | | | | | | | | | | |
| 1   5               10                  15 | | | | | | | | | | | | | | | | |
| tat gaa tac ggt tct gac ttt cct ccg ttt gtc atc gat aaa gtc ggc | | | | | | | | | | | | | | | | 96 |
| Tyr Glu Tyr Gly Ser Asp Phe Pro Pro Phe Val Ile Asp Lys Val Gly | | | | | | | | | | | | | | | | |
|         20                  25                  30 | | | | | | | | | | | | | | | | |
| act aag tgt tca atg aac aac agc gcg gta aga acg gtt gac ctg aac | | | | | | | | | | | | | | | | 144 |
| Thr Lys Cys Ser Met Asn Asn Ser Ala Val Arg Thr Val Asp Leu Asn | | | | | | | | | | | | | | | | |
|     35                  40                  45 | | | | | | | | | | | | | | | | |
| ggc tca act tca ggt aac acc act tac agc tat acc tgt aac gac tca | | | | | | | | | | | | | | | | 192 |
| Gly Ser Thr Ser Gly Asn Thr Thr Tyr Ser Tyr Thr Cys Asn Asp Ser | | | | | | | | | | | | | | | | |
| 50                  55                  60 | | | | | | | | | | | | | | | | |
| acc aac tac aac gat tac aaa gcc att aac ggc gcg tac tcg cca ctg | | | | | | | | | | | | | | | | 240 |
| Thr Asn Tyr Asn Asp Tyr Lys Ala Ile Asn Gly Ala Tyr Ser Pro Leu | | | | | | | | | | | | | | | | |
| 65              70                  75                  80 | | | | | | | | | | | | | | | | |
| aac gat gcc cac tac ttc ggt aaa gtg gtt ttc gat atg tac aaa gac | | | | | | | | | | | | | | | | 288 |
| Asn Asp Ala His Tyr Phe Gly Lys Val Val Phe Asp Met Tyr Lys Asp | | | | | | | | | | | | | | | | |
|                 85                  90                  95 | | | | | | | | | | | | | | | | |
| tgg atg aac acc aca cca ctg acg ttc cag ctg act atg cgt gtt cac | | | | | | | | | | | | | | | | 336 |
| Trp Met Asn Thr Thr Pro Leu Thr Phe Gln Leu Thr Met Arg Val His | | | | | | | | | | | | | | | | |
|             100                 105                 110 | | | | | | | | | | | | | | | | |
| tat ggt aac aac tac gaa aac gcg ttc tgg aat ggt tca tcc atg acc | | | | | | | | | | | | | | | | 384 |
| Tyr Gly Asn Asn Tyr Glu Asn Ala Phe Trp Asn Gly Ser Ser Met Thr | | | | | | | | | | | | | | | | |
|         115                 120                 125 | | | | | | | | | | | | | | | | |
| ttc ggt gat ggc tac agc acc ttc tac ccg ctg gtg gat att aac gtt | | | | | | | | | | | | | | | | 432 |
| Phe Gly Asp Gly Tyr Ser Thr Phe Tyr Pro Leu Val Asp Ile Asn Val | | | | | | | | | | | | | | | | |
|     130                 135                 140 | | | | | | | | | | | | | | | | |
| agt gcc cac gaa gtg agc cac ggt ttc acc gaa caa aac tcg ggt ctg | | | | | | | | | | | | | | | | 480 |
| Ser Ala His Glu Val Ser His Gly Phe Thr Glu Gln Asn Ser Gly Leu | | | | | | | | | | | | | | | | |
| 145                 150                 155                 160 | | | | | | | | | | | | | | | | |
| gtg tac gag aat atg tct ggt ggt atg aac gaa gcg ttc tct gat att | | | | | | | | | | | | | | | | 528 |
| Val Tyr Glu Asn Met Ser Gly Gly Met Asn Glu Ala Phe Ser Asp Ile | | | | | | | | | | | | | | | | |
|                 165                 170                 175 | | | | | | | | | | | | | | | | |
| gca ggt gaa gca gca gag ttc tac atg aaa ggc agc gtt gac tgg gtt | | | | | | | | | | | | | | | | 576 |
| Ala Gly Glu Ala Ala Glu Phe Tyr Met Lys Gly Ser Val Asp Trp Val | | | | | | | | | | | | | | | | |
|             180                 185                 190 | | | | | | | | | | | | | | | | |
| gtc ggt gcg gat atc ttc aaa tca tcc ggc ggt ctg cgt tac ttt gat | | | | | | | | | | | | | | | | 624 |
| Val Gly Ala Asp Ile Phe Lys Ser Ser Gly Gly Leu Arg Tyr Phe Asp | | | | | | | | | | | | | | | | |
|         195                 200                 205 | | | | | | | | | | | | | | | | |
| cag cct tcg cgt gac ggc cgt tct atc gac cat gcg tct gac tac tac | | | | | | | | | | | | | | | | 672 |
| Gln Pro Ser Arg Asp Gly Arg Ser Ile Asp His Ala Ser Asp Tyr Tyr | | | | | | | | | | | | | | | | |
|     210                 215                 220 | | | | | | | | | | | | | | | | |
| aat ggc ctg aat gtt cac tac tca agt ggt gta ttc aac cgt gcg ttc | | | | | | | | | | | | | | | | 720 |
| Asn Gly Leu Asn Val His Tyr Ser Ser Gly Val Phe Asn Arg Ala Phe | | | | | | | | | | | | | | | | |

```
                225                 230                 235                 240
tac ctg ctg gct aac aaa gcg ggt tgg gat gta cgc aaa ggc ttt gaa     768
Tyr Leu Leu Ala Asn Lys Ala Gly Trp Asp Val Arg Lys Gly Phe Glu
                245                 250                 255 gtg ttt acc ctg gct aac caa ttg tac tgg aca gcg aac agc aca ttt     816
Val Phe Thr Leu Ala Asn Gln Leu Tyr Trp Thr Ala Asn Ser Thr Phe
                260                 265                 270 gat gaa ggc ggt tgt ggt gta gtg aaa gct gcg agc gac atg ggt tac     864
Asp Glu Gly Gly Cys Gly Val Val Lys Ala Ala Ser Asp Met Gly Tyr
            275                 280                 285 agc gtt gca gac gta gaa gat gcg ttt aac acg gta ggc gtt aac gcg     912
Ser Val Ala Asp Val Glu Asp Ala Phe Asn Thr Val Gly Val Asn Ala
        290                 295                 300 tct tgt ggt gca act cct cct ccg tct ggc gat gta ctg gaa atc ggt     960
Ser Cys Gly Ala Thr Pro Pro Pro Ser Gly Asp Val Leu Glu Ile Gly
305                 310                 315                 320 aaa ccg ctg gcg aac ctt tca ggt aac cgc aat gac atg act tac tac    1008
Lys Pro Leu Ala Asn Leu Ser Gly Asn Arg Asn Asp Met Thr Tyr Tyr
                325                 330                 335 acg ttc aca cca agc agc tca tct agc gta gtg att aag atc act ggc    1056
Thr Phe Thr Pro Ser Ser Ser Ser Ser Val Val Ile Lys Ile Thr Gly
                340                 345                 350 ggt aca ggt gat gca gac ctt tac gtg aaa gcg ggt agc aag cca acc    1104
Gly Thr Gly Asp Ala Asp Leu Tyr Val Lys Ala Gly Ser Lys Pro Thr
            355                 360                 365 acg act tct tac gat tgc cgt cca tat aag tat ggt aac gaa gag cag    1152
Thr Thr Ser Tyr Asp Cys Arg Pro Tyr Lys Tyr Gly Asn Glu Glu Gln
        370                 375                 380 tgt tca att tca gcg caa gcg ggt act acg tat cac gtt atg ctg cgt    1200
Cys Ser Ile Ser Ala Gln Ala Gly Thr Thr Tyr His Val Met Leu Arg
385                 390                 395                 400 ggt tac agc aat tac gct ggt gta act ttg cgt gct gac taa            1242
Gly Tyr Ser Asn Tyr Ala Gly Val Thr Leu Arg Ala Asp
                405                 410

<210> SEQ ID NO 18
<211> LENGTH: 413
<212> TYPE: PRT
<213> ORGANISM: Vibrio proteolyticus

<400> SEQUENCE: 18

Ala Gln Ala Asp Gly Thr Gly Pro Gly Gly Asn Thr Lys Thr Gly Arg
1               5                   10                  15

Tyr Glu Tyr Gly Ser Asp Phe Pro Pro Phe Val Ile Asp Lys Val Gly
            20                  25                  30

Thr Lys Cys Ser Met Asn Asn Ser Ala Val Arg Thr Val Asp Leu Asn
        35                  40                  45

Gly Ser Thr Ser Gly Asn Thr Thr Tyr Ser Tyr Thr Cys Asn Asp Ser
    50                  55                  60

Thr Asn Tyr Asn Asp Tyr Lys Ala Ile Asn Gly Ala Tyr Ser Pro Leu
65                  70                  75                  80

Asn Asp Ala His Tyr Phe Gly Lys Val Val Phe Asp Met Tyr Lys Asp
                85                  90                  95

Trp Met Asn Thr Thr Pro Leu Thr Phe Gln Leu Thr Met Arg Val His
            100                 105                 110

Tyr Gly Asn Asn Tyr Glu Asn Ala Phe Trp Asn Gly Ser Ser Met Thr
        115                 120                 125

Phe Gly Asp Gly Tyr Ser Thr Phe Tyr Pro Leu Val Asp Ile Asn Val
    130                 135                 140
```

```
Ser Ala His Glu Val Ser His Gly Phe Thr Glu Gln Asn Ser Gly Leu
145                 150                 155                 160

Val Tyr Glu Asn Met Ser Gly Gly Met Asn Glu Ala Phe Ser Asp Ile
            165                 170                 175

Ala Gly Glu Ala Ala Glu Phe Tyr Met Lys Gly Ser Val Asp Trp Val
            180                 185                 190

Val Gly Ala Asp Ile Phe Lys Ser Ser Gly Gly Leu Arg Tyr Phe Asp
            195                 200                 205

Gln Pro Ser Arg Asp Gly Arg Ser Ile Asp His Ala Ser Asp Tyr Tyr
            210                 215                 220

Asn Gly Leu Asn Val His Tyr Ser Ser Gly Val Phe Asn Arg Ala Phe
225                 230                 235                 240

Tyr Leu Leu Ala Asn Lys Ala Gly Trp Asp Val Arg Lys Gly Phe Glu
            245                 250                 255

Val Phe Thr Leu Ala Asn Gln Leu Tyr Trp Thr Ala Asn Ser Thr Phe
            260                 265                 270

Asp Glu Gly Gly Cys Gly Val Val Lys Ala Ala Ser Asp Met Gly Tyr
            275                 280                 285

Ser Val Ala Asp Val Glu Asp Ala Phe Asn Thr Val Gly Val Asn Ala
            290                 295                 300

Ser Cys Gly Ala Thr Pro Pro Pro Ser Gly Asp Val Leu Glu Ile Gly
305                 310                 315                 320

Lys Pro Leu Ala Asn Leu Ser Gly Asn Arg Asn Asp Met Thr Tyr Tyr
            325                 330                 335

Thr Phe Thr Pro Ser Ser Ser Ser Val Val Ile Lys Ile Thr Gly
            340                 345                 350

Gly Thr Gly Asp Ala Asp Leu Tyr Val Lys Ala Gly Ser Lys Pro Thr
            355                 360                 365

Thr Thr Ser Tyr Asp Cys Arg Pro Tyr Lys Tyr Gly Asn Glu Glu Gln
            370                 375                 380

Cys Ser Ile Ser Ala Gln Ala Gly Thr Thr Tyr His Val Met Leu Arg
385                 390                 395                 400

Gly Tyr Ser Asn Tyr Ala Gly Val Thr Leu Arg Ala Asp
            405                 410
```

METHOD FOR PRODUCING AMINOPEPTIDASE

TECHNICAL FIELD

The present invention relates to a method for production of an aminopeptidase, and in particular to an improved method for production of an aminopeptidase utilizing *E. coli*.

BACKGROUND ART

Since recombinant DNA technology was established in 1980s, eukaryotic simple proteins have been widely produced utilizing *E. coli*, which allows low-cost production. In living bodies in which they naturally occur, many proteins are first synthesized in the forms of inactive, precursor proteins, and then they undergo cleavage by proteolytic enzymes (e.g., removal of the methionine at their amino-terminus (N-terminus)), or other processing, to form mature proteins. Eukaryotic proteins produced by *E. coli*, which is a prokaryote, however, often have one or more unnecessary amino acid residues, such as methionine, which originates from the start codon and is left on their N-terminus. A protein having such one or more unnecessary amino acid residues might provoke an antigen-antibody reaction such as anaphylaxis if it is administered to a human as a medicine. Therefore, such unnecessary amino acid residues should be removed.

Among aminopeptidases, which are enzymes having an activity to cleave amino acid residues one by one starting with the amino-terminus (N-terminus) of a protein, various types are known which differ from one another, e.g., in their specificity. Thus, there have been reports on methods for converting precursor proteins to their corresponding mature proteins utilizing aminopeptidases (e.g., Patent document 1, Patent document 2, and Patent document 3).

For example, human growth hormone, when produced using recombinant *E. coli*, is obtained in the form of a precursor human growth hormone having a methionine residue which is left on its N-terminus, and thus its amino acid sequence goes, starting from the N-terminus, as "Met-Phe-Pro- . . . " and so on. Among aminopeptidases, those which have a property that their reaction of cleaving peptide bonds stops one residue before proline in a protein can selectively remove methionine alone at the N-terminus of the precursor human growth hormone. It is well known that human mature growth hormone can be obtained from precursor human growth hormone by using such an aminopeptidase, and pharmaceutical preparations containing human mature growth hormone produced by such a method are currently supplied to the pharmaceutical market.

Various aminopeptidases have been known so far which are suitable for removal of N-terminal methionine like the one that is included in human precursor growth hormone (Patent document 4, Patent document 5). One of such aminopeptidases is an aminopeptidase of *Vibrio proteolyticus*. This enzyme is produced by translation in the form of a preproprotein consisting of four domains (signal peptide, N-terminal propeptide, mature region, and C-terminal propeptide). The aminopeptidase of *V. proteolyticus* provides advantages that it is found in the culture medium in which *V. proteolyticus* has been cultured for a certain length of time, and that it then can be easily isolated from the cells by, e.g., centrifugation. However, it has a great disadvantage that because the amount of aminopeptidase found in such a culture medium is small, a large facility would be required in order to produce aminopeptidase as needed by the industry, and this would prove costly. Thus, studies have been carried out to modify the *V. proteolyticus* aminopeptidase gene to adapt it for expression in *E. coli*, by, e.g., replacing its secretion signal with PelB, and thus to let the aminopeptidase be produced and secreted by *E. coli*. However, the production efficiency of such a method has still been at most about threefold in comparison with the case where *V. proteolyticus* itself is used.

In general, aminopeptidases (AP), after once produced by translation in an inactive form, are converted to active ones, the mechanism of which has not been fully clarified though. It is known that in some species close to *V. proteolyticus*, AP is converted to its active form through cleavage by some kind of protease (Non-patent document 1, Non-patent document 2). Again, a neutral protease [vibriolysin: nprV] has been discovered in a culture medium of *V. proteolyticus* (Non-patent document 3, Non-patent document 4, Non-patent document 5). Vibriolysin is an extracellular zinc metalloprotease, which is produced by translation in the form of a peptide chain composed of a signal peptide consisting of amino acids 1-24, N-terminal peptide consisting of amino acids 25-196, and the remaining amino acids 197-609 forming the mature protein. The role of vibriolysin in connection with the production of the aminopeptidease in V, proteolyticus has not been made clear.

[Patent document 1] Japanese Patent Application Publication No. H62-244381

[Patent document 2] Japanese Patent Application Publication No. H62-500003

[Patent document 3] Japanese Patent Application Publication No. 2004-533263

[Patent document 4] WO 86/01229

[Patent document 5] U.S. Pat. No. 5,569,598

[Non-patent document 1] S. Nirasawa et al. (1999) Biochim Biophys Acta. August 17; 1433(1-2):335-42

[Non-patent document 2] Z Z. Zhang et al. (2000) Biochem J. September 15; 350 Pt 3:671-6

[Non-patent document 3] J. Prescott et al. (1976) Methods Enzymol. 45 404-415

[Non-patent document 4] D. Durham (1990) Appl Environ Microbial. August; 56(8):2277-81

[Non-patent document 5] S. Shinoda et al. (2004) Handbook of Proteolytic Enzymes 2nd ed., 399-40

DISCLOSURE OF THE INVENTION

Problem to be Solved by the Invention

Against the above background, the objective of the present invention is to provide a method for production of an aminopeptidase with improved efficiency.

Means to Solve the Problem

By allowing *V. proteolyticus* aminopeptidase gene and vibriolysin (nprV) gene, a neutral protease occurring in the same bacteria, to co-express in *E. coli*, the present inventors succeeded in obtaining an aminopeptidase in the culture supernatant with higher efficiency than had been possible using transformant *E. coli* cells. Furthermore, by modifying the nucleotide sequence of nprV gene, the present inventors succeeded in letting such transformant *E. coli* cells steadily produce the aminopeptidase with strikingly high efficiency and secrete it out of the cells. The present invention was completed based on these findings.

Thus the present invention provides what follows.

1. A method for production of an aminopeptidase comprising the steps of:

either transforming host bacteria with an aminopeptidase gene and with a neutral protease gene, or transforming some part of host bacteria with an aminopeptidase gene while transforming the other part of the host bacteria with a neutral protease gene, culturing in a medium the host bacteria transformed with the aminopeptidase gene and with the neutral protease gene, or culturing a mixture of the host bacteria transformed with the aminopeptidase gene and the host bacteria transformed with the neutral protease gene, to let both the aminopeptidase gene and the neutral protease gene be expressed, and collecting the aminopeptidase thus produced from the culture mixture.

2. The method for production according to 1 above, wherein the process of collecting the aminopeptidase includes collecting the aminopeptidase released into the culture supernatant.

3. The method for production according to 1 or 2 above, wherein each of the aminopeptidase gene and the neutral protease gene is a gene originating from bacteria which belong to a species different from the species to which the host bacteria belong.

4. The method for production according to one of 1 to 3 above, wherein the aminopeptidase gene and the neutral protease gene both originate from bacteria which belong to one and the same species.

5. The method for production according to one of 1 to 4 above, wherein the aminopeptidase gene is a gene for an aminopeptidase which has a characteristic that the peptide bond-cleaving reaction caused by the aminopeptidase stops one residue before a proline residue.

6. The method for production according to one of 1 to 5 above, wherein the aminopeptidase gene and the neutral protease gene both originate from *V. proteolyticus*.

7. The method for production according to one of 1 to 6 above, wherein the host bacteria are *E. coli*.

8. The method for production according to one of 1 to 7 above, wherein the aminopeptidase, while in the form of the preproprotein thereof, has the amino acid sequence defined as SEQ ID NO:4.

9. The method for production according to one of 1 to 8 above, wherein the neutral protease is vibriolysin.

10. The method for production according to one of 1 to 9 above, wherein the vibriolysin, in the form of the mature protein thereof, has the amino acid sequence defined as SEQ ID NO:18.

11. The method for production according to one of 1 to 9 above, the vibriolysin gene carries a mutation within the N-terminal peptide region thereof.

12. The method for production according to one of 1 to 11 above, wherein the mutation is a mutation of Ala to Val occurring at the 158th amino acid residue within the N-terminal peptide region.

13. A vibriolysin gene comprising, as the nucleotide which encodes vibriolysin propeptide, the nucleotide sequence defined as SEQ ID NO:15.

14. The vibriolysin gene according to 13 above comprising the nucleotide sequence defined as SEQ ID NO:15 and the nucleotide sequence defined as SEQ ID NO:17 which follows the former.

15. The vibriolysin gene according to 14 above comprising a nucleotide sequence encoding a signal sequence, the nucleotide sequence defined as SEQ ID NO:15 which follows the former, and the nucleotide sequence defined as SEQ ID NO:17 which follows the letter.

16. A plasmid which is an expression vector for *E. coli* for expression of vibriolysin comprising the DNA according to one of 13 to 15 above.

17. An *E. coli* cell which has been transformed through introduction of a vibriolysin gene and an aminopeptidase gene originating from *V. proteolyticus* so that the cell expresses both of the genes.

18. The *E. coli* cell according to 17 above, wherein the vibriolysin gene carries in the propeptide region thereof a mutation which brings about a mutation in an amino acid residue.

19. An *E. coli* cell which has been transformed through introduction of the plasmid according to 16 above and another plasmid which is an expression vector comprising an aminopeptidase gene originating from *V. proteolyticus*.

Effect of the Invention

The present invention enables to let host bacteria, especially *E. coli*, produce an aminopeptidase, in particular an aminopeptidase originating *V. proteolyticus*, more efficiently than before and release the enzyme into the culture medium. In particular, when a neutral protease originating from *V. proteolyticus* is employed as the neutral protease which is to be co-expressed with the aminopeptidase, the present invention greatly increases the efficiency of aminopeptidase production into the culture medium, and further, through introduction of a mutation into the amino acid sequence of the neutral protease, dramatically increases the production efficiency.

BEST MODE FOR CARRYING OUT THE INVENTION

Figure 1:
FIG. 1 shows the recombinant portions of (a) vector pRL-AP, (b) vector pET-AP, and (c) vector pCDF-nprV.
Figure 1:
Figure 1:

In the present invention, when transforming host bacteria with genes for an aminopeptidase and a neutral protease, an expression vector comprising an aminopeptidase gene and another expression vector comprising a neutral protease gene may be introduced together into the same host bacteria to transform them. Alternatively, host bacteria may be transformed with an expression vector comprising both an aminopeptidase gene and a neutral protease gene. Furthermore, it is also possible to introduce an expression vector comprising an aminopeptidase gene into some part of the bacteria to transform them while introducing an expression vector comprising a neutral protease gene into the other part of the bacteria to transform them. In this last case, the two types of host bacteria, respectively transformed with either one or the other gene alone, are mixed before their culture for expression of each of the genes.

While one of a variety of aminopeptidases known to those skilled in the art may be employed, particularly preferred is an aminopeptidase originating from *V. proteolyticus*.

While one of a variety of neutral peptidases known to those skilled in the art may be employed, particularly preferred is a neutral protease originating from *V. proteolyticus*.

While a variety of bacteria may be used as host bacteria, *E. coli* is preferred, for it is low cost and easy to handle.

In the present invention, the term "vibriolysin gene" includes not only the wild-type gene (SEQ ID NO:1) but also genes which carry mutations in part insofar as they do not adversely affect the expression of the enzymatic activity of vibriolysin. Mutations in amino acids may include insertion, substitution, deletion and addition, and the number of amino acids that undergo mutation may, in general, be one to several (e.g., 1 to 5). In particular, introducing an amino acid mutation in the N-terminal peptide region of vibriolysin may give a favorable effect for steady expression of vibriolysin in its active form in *E. coli*. A mutation in the amino acid sequence of vibriolysin may be introduced by inducing a mutation in the nucleotide sequence of the gene for the protein. It is possible to introduce a mutation into a gene, either at an aimed position or randomly, employing well known techniques. By introducing into host bacteria respective vibriolysin genes having an induced mutation together with an aminopeptidase gene to transform them, and measuring the amount of active aminopeptidase produced after culturing the host bacteria to let both genes be expressed, vibriolysin mutants enabling the higher production of aminopeptidase may be selected with ease.

EXAMPLES

While the present invention will be described in further detail below referring to examples, it is not intended that the present invention be limited to the examples.

Reference Example 1

Production of Aminopeptidase Using Transformant *E. coli*

Genome DNA was prepared from *V. proteolyticus*, and aminopeptidase (AP) gene was cloned in the following manner.

(1) Cloning of Aminopeptidase Gene

Using "GenElute Bacterial Genomic DNA kit" (Sigma, No. NA2100), genome DNA was extracted from 3.0 mL of the culture of *V. proteolyticus* cells which had been cultured overnight (14 hrs) at 26° C. in a medium containing 0.8% Nutrient Broth (Difco, No. 234000) and 3.0% NaCl (for specific procedures, the instruction included in the kit was followed). Using the genome DNA thus extracted as a template, aminopeptidase (AP) gene was amplified by PCR using two primers (below) (reaction conditions: 94° C.: 2 min, then 30 cycles of 94° C.: 15 sec, 55° C.: 30 sec, and 68° C.: 90 sec; and then 68° C.: 7 min), and the amplification product thus obtained was ligated to the cloning vector pGEM-T easy (mftd. by Promega).

```
primer BaRBFL41:
                                        (SEQ ID NO: 1)
CGGGATCCTAAGGAGGTTATCATATGAAATATACCAAAACG
("GGATCC" at nucleotides 3-8 constitutes a
BamHI site)

primer No-FL33R:
                                        (SEQ ID NO: 2)
CGGCGGCCGCTTATCAGAAAGTGCTGGCTTTCA
("GCGGCCGC" at nucleotides 3-10 constitutes a
NotI site)
```

Using the reaction mixture, competent *E. coli* cells were transformed, and from one of the colonies thus formed, the plasmid was extracted. The DNA sequence of this plasmid was analyzed and confirmed to contain no error in the sequence. The nucleotide sequence of AP gene and the amino acid sequence corresponding thereto are shown as SEQ ID NO:3 and SEQ ID NO:4, respectively.

(2) Replacement of Secretion Signal Sequence

Then, the secretion signal sequence of AP gene was replaced with the PelB secretion signal sequence of *Erwinia carotovora*. First, the PelB secretion signal sequence was constructed by bonding four oligonucleotides (shown below) with one another. Specifically, the following single-strand DNAs (i) Pelb-1F and (ii) Pelb-2R, as well as (iii) Pelb-3F and (iv) PelB-4R were subjected to PCR, respectively, and both PCR amplification products then were attached to each other and subjected to PCR to form the PelB secretion signal sequence (PCR conditions: 94° C.: 2 min; then 98° C.: 10 sec, 55° C.: 30 sec, 68° C.: 30 sec. Five cycles in the first reaction, and 35 cycles in the second reaction). The 5'-terminal portion of the AP gene was replaced with this PelB secretion signal sequence (utilizing BamHI/MunI site) to form a PelB-AP sequence.

```
(i) PelB-1F:
                                        (SEQ ID NO: 5)
ACGGGATCCTAAGGAGGTTATCATATGAAATACCTGCTGCCCAC (ii) PelB-2R:
                                        (SEQ ID NO: 6)
CAGGAGCAGCAGACCAGCAGCAGCGGTGGGCAGCAGGTATTTCAT (iii) PeIB-3F:
                                        (SEQ ID NO: 7)
GCTGGTCTGCTGCTCCTGGCTGCCCAACCCGCGATGGCCGAAG (iv) PELB-4R:
                                        (SEQ ID NO: 8)
CGCACCAATTGAGATCCACACTTTGTCTTCGGCCATCGCGGGTT
```

The nucleotide sequence (63 bases) for the original secretion signal is shown as SEQ ID NO:9, and the nucleotide sequence (66 bases) for the PelB secretion signal with which the former was replaced is shown as SEQ ID NO:10, respectively.

(3) Incorporation of PelB-AP into Vector pRL.

Figure 2:
FIG. 2 is a gene map for vector pRL-PelB-AP.
Figure 2:
Figure 2:

The AP-gene thus obtained whose secretion signal had been replaced with PelB secretion signal (PelB-AP) was cloned into vector pRL, which has a temperature-dependent pRL promoter, to construct an AP expression vector, "pRL-AP" (FIG. 1). Namely, plasmid pCE30 (ATCC37830) (Elvin C M et al., 1990, Gene 87, 123-126) was purchased from ATCC. This plasmid is constructed so that it has, upstream of the cloning site, the pL promoter of λ phage, the pR promoter arranged in tandem therewith and, further upstream of them, the nucleotide sequence of λc1857, a temperature-sensitive repressor gene, and that transcription of the promoter is suppressed at 30° C., and an incorporated gene is expressed if culture is done at 42° C. This plasmid was modified to include NotI site immediately after the λ promoter to obtain vector pRL. Vector pRL was digested in advance with BamHI and NotI, and its vector region was purified. PelB-AP sequence was also digested in the same manner and the sequence thus formed was purified. These DNA fragments were ligated, and with thus obtained DNA, E. coli cells which had been made competent were transformed to let them form colonies. A plasmid was extracted from a colony, and through cleavage with restriction enzymes and sequencing which followed, its sequence was determined. The plasmid thus obtained was named pRL-PelB-AP (FIG. 2).

To 18 μL of the competent cells (*E. coli* BL21 strain) was added 2 μL of the pRL-PelB-AP plasmid solution. This mixture was let stand on ice for 30 minutes, then heat treated at 42° C. for 18 seconds, and a LB+ampicillin (Amp) plate was inoculated with this and was let stand overnight at 30° C. A colony was chosen at random and shake cultured (200 rpm) in LB medium containing 100 μg/mL Amp for overnight at 30° C. For induction of expression, this culture mixture, which had been cultured overnight, was diluted 10 fold with LB+Amp medium, shake cultured (200 rpm) at 30° C. for 3 hours, and then after its temperature was raised to 40° C. or 42° C., cultured for further 4.5 hours. The culture mixture was centrifuged at 12000 rpm for 5 minutes to separate the supernatant and the precipitate. The supernatant then was subjected to measurement of enzymatic activity and the like as described below, and the precipitate was subjected to the following process to extract the enzyme.

(4) Extraction of the Enzyme

To the precipitate was added ⅕ volume of BugBuster (Takara Bio) and the mixture, after gently stirred at room temperature for 10 minutes, was centrifuged at 15000 rpm for 10 minutes to separate the supernatant and the precipitate. The supernatant was subjected, as the cell lysate, to measurement of enzyme activity.

(5) Measurement of AP Enzymatic Activity

Figure 3:
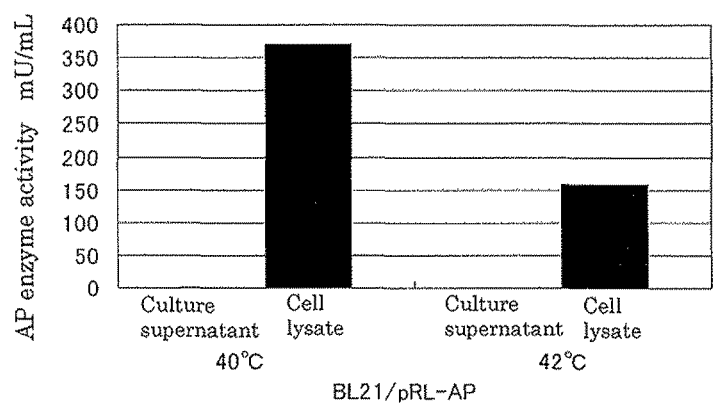
FIG. 3 is a graph showing aminopeptidase activity (AP enzyme activity) in the culture supernatant and in the cell lysate, respectively, after expression of BL21/pRL-AP was induced at 40° C. and 42° C.

The enzymatic activity of the AP thus obtained was measured using a synthetic substrate (L-pNA). Using as a guide the methods described in J. Prescott et al. (1971) J. Biol. Chem. 246(6)1756-1764 and J. Prescott et al. (1976) Methods Enzymol. 45 530-543, measurement was carried out as follows. First, 10 μL of the sample was added to 100 μL of the substrate solution [50 mM Tris HCl containing 1 mM leucine-p-nitroanilide (Sigma, L-2158), 0.5 mM Tricine (N-[tris(hydroxymethyl)methyl]glycine), 5 μM zinc sulfate (pH 8.0)], and reaction was allowed at room temperature for 30 minutes. After 300 μL of a stop solution (0.1 M HCl) was added to this and mixed, 100 μL of the mixture solution was transferred to a 96-well plate, and was read for OD (405 nm) on a plate reader (Table 1). Separately, a calibration curve was produced using an aminopeptidase (Sigma, A-8200) as a standard, and the AP activity was determined for each sample. As a result, AP activity was detected in the cell extract as shown in FIG. 3, while almost no activity was detected in the culture supernatant.

TABLE 1

| | Aminopeptidase | |
|---|---|---|
| | | (Unit: mU/mL) |
| | 40° C. | 42° C. |
| Culture supernatant | Below detection limit | Below detection limit |
| Cell lysate | 370.5 | 158.2 |

(6) Cloning of PelB-Substituted AP Gene into pET

Figure 4:
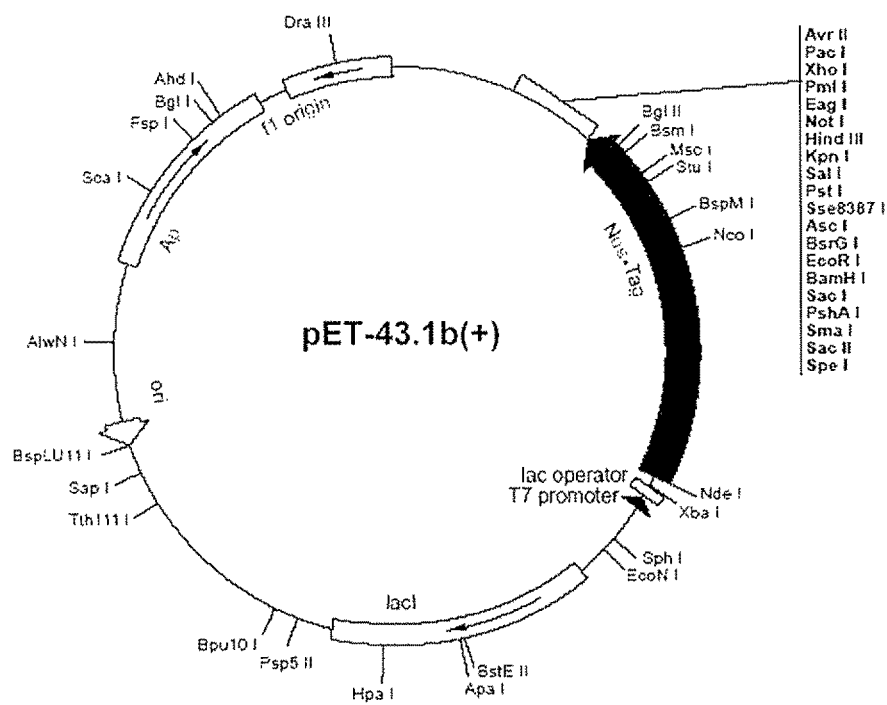
FIG. 4 is a gene map for vector pET-43.1b(+)

In general, it is thought that culture at the lower temperatures is advantageous for secretory expression. Therefore, in order to examine induction at the lower temperatures, the PelB-substituted AP gene was cloned into vector pET, which has T7 promoter, to form an AP expression vector, "pET-AP" (FIG. 1). Namely, pET-43.1b(+) (Novagen, 70940-3) (FIG. 4) was purchased from Merck & Co., digested with NdeI and NotI, and its Nus-tag portion was then removed, and the vector region was purified. The pRL-PelB-AP, which had been prepared in advance, was also digested likewise with NdeI and NotI, and its PelB-AP was purified. Both fragments were ligated, and JM1.09 was transformed with this ligation product to form colonies. Plasmid was prepared from colonies randomly chosen, and a proper clone was selected through restriction enzyme treatment using NdeI and NotI. The plasmid thus obtained was named pET-AP.

(7) Expression of AP

The pET-AP thus obtained was introduced into *E. coli* BL21(DE3) strain, which then was induced to express AP with 1 mM IPTG at the temperature condition of 25° C. Namely, 1 μL of pET-AP solution was added to 50 μL of BL21-star(DE3) competent cells (Invitrogen, C6010-03), and the mixture, after let stand on ice for 30 minutes, was heat treated at 42° C. for 30 seconds. LB+ampicillin (Amp) plates were inoculated with the mixture, and let stand at 30° C. overnight. Colonies were chosen at random, and shake cultured (220 rpm) in LB medium containing 100 μg/mL Amp at 30° C. for 16 hours. The culture was diluted 20-fold with LB medium, and after a further shake culture at 30° C. for 3 hours (220 rpm), IPTG was added to the final concentration of 1 mM, and the mixture was shake cultured for further 16-20 hours at 25° C. (220 rpm). The culture was centrifuged at 3000 rpm for 30 minutes, and the supernatant was subjected to measurement of AP enzyme activity.

(8) Measurement of AP Enzyme Activity

The AP enzyme activity was measured in the same manner as described in (5) above, giving the following results.

TABLE 2

| Aminopeptidase activity | |
|---|---|
| | (Unit: mU/mL) |
| Culture supernatant | 141.4 |
| Cell lysate | 1485.7 |

Figure 5:
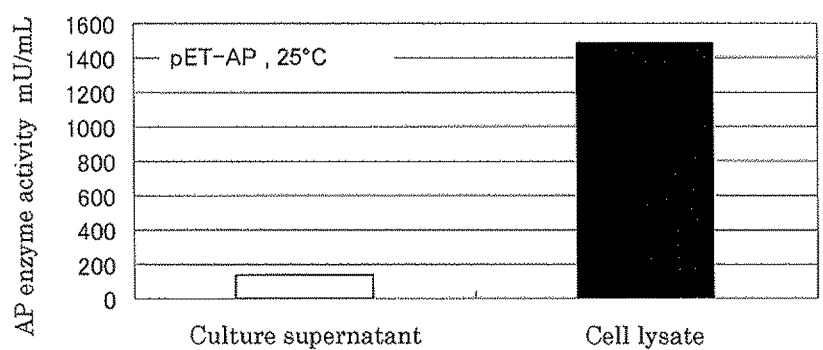
FIG. 5 is a graph showing the aminopeptidase activity (AP enzyme activity) in the culture supernatant and in the cell lysate, respectively, after expression of BL21(DE3)/pET-AP was induced with 1 mM IPTG at 25° C.

As seen in Table 2, high AP activity was observed in the culture, which was around 3 times higher than observed in the case where *V. proteolyticus* was used. However, according to this system, it was only less than 10% of total AP activity that was secreted in the culture medium, while not less than 90% was not secreted but found in the cell lysate (FIG. 5). This results were similar to those so far reported in scientific literatures, failing to efficiently obtain AP activity in the culture medium.

Example 1

Co-Expression of Neutral Protease and Aminopeptidase

The present inventors attempted to let nprV and AP co-express in *E. coli* in the following manner.

(1) Cloning of Vibriolysin (nprV) Gene

The nucleotide sequence encoding the neutral protease nprV (preprotein) is shown as SEQ ID NO:11, and the corresponding amino acid sequence as SEQ ID NO:12, respectively. In SEQ ID NO:11, nucleotides 1-72 encode the signal sequence, nucleotides 73-588 the propeptide sequence, and nucleotides 589-1830 the mature protein, respectively. In SEQ ID NO:12, amino acids 1-24 constitute the signal sequence, amino acids 25-196 the propeptide, and amino acids 197-609 the protein claimed herein, respectively.

Using the genome DNA prepared in the section "(1) Cloning of aminopeptidase gene" as a template, nprV gene was cloned by PCR in the following manner. PCR was performed using Blend Taq-plus (TOYOBO, BTQ-201). The oligonucleotides of the following sequences were used as primers.

(i) nprV_NcoI_FW primer
(5'-GCATAATCCATGGCAAAATAAAACACAACGTCAC-

ATCAACTGGC-3': SEQ ID NO: 13, nucleotides 8-13, CCATGG, providing a NcoI site)

(ii) nprV_NotI_BamHI_RV primer
(5'-GCATAATGCGGCCGCGGATCCATTAGTC-

AGCACGCAAAGTTACACC-3': SEQ ID NO: 14, nucleotides 8-22, providing NotI and BamHI sites)

The condition for the reaction consisted of [94° C./2 min, (94° C./30 sec, from 60 to 54° C. (−1° C./cycle)/30 see, 72° C./2.5 min)×7 cycles, (94° C./30 sec, 53° C./30 sec, 72° C./2.5 min)×30 cycles, 4° C./∞]

(2) Construction of Expression Vector pCDF-nprV

Figure 6:
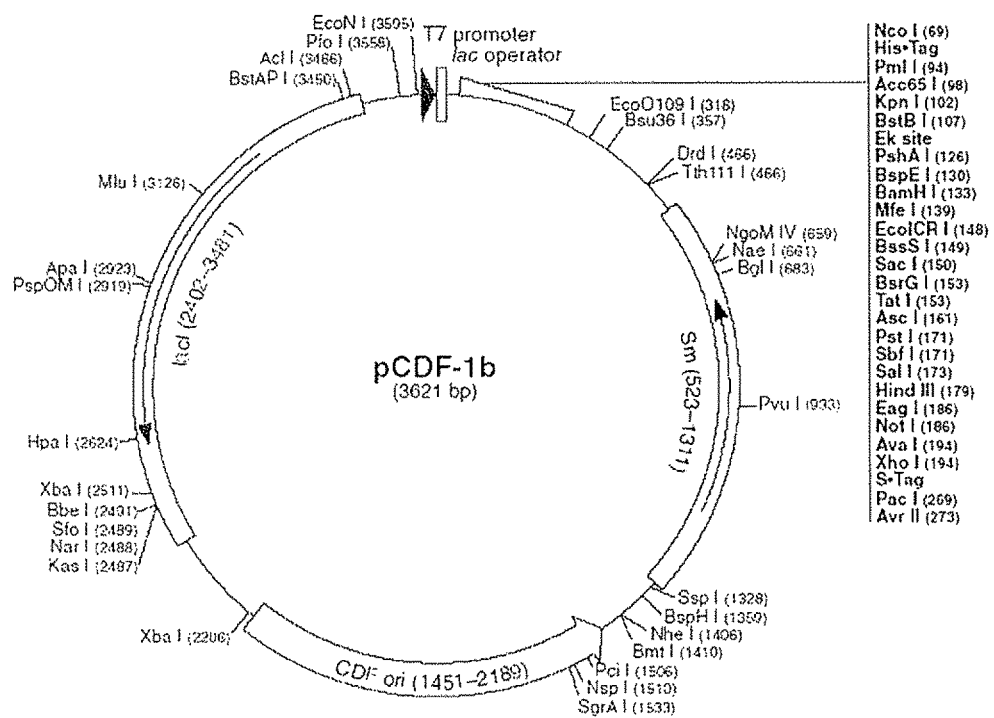
FIG. 6 is a gene map for vector pCDF-1b.

The cloned nprV gene (having inserted "GCA" (encoding Ala) immediately after the start codon "ATG" to introduce an NcoI site) was cloned under T7 promoter to form an nprV expression vector, "pCDF-nprV" (FIG. 1). Namely, pCDF-1b (Novagen, 71330-3) (FIG. 6) was purchased from Merck & Co. This plasmid and the nprV gene PCR product prepared above were separately digested with NcoI and NotI. After they were separately purified, both fragments were ligated to each other, and with the ligation product thus obtained, JM109 was transformed to let them form colonies. Plasmid was prepared from colonies chosen at random, and proper clone was selected through restriction enzyme treatment using NcoI and NotI. The nucleotide sequence was analyzed and it was confirmed that the sequence was free of mutation. The plasmid thus obtained was named pCDR-nprV.

(3) Co-Expression of Vibriolysin and Aminopeptidase in *E. coli*

This expression vector and the aforementioned vector pET-AP were introduced into the *E. coli* cells of the BL21(DE3) strain, and the cells were induced to express AP and nprV with 1 mM IPTG at 25° C. BL21star(DE3)/pET-AP produced in the section "(6) Cloning of PelB-substituted AP gene into pET" was prepared as competent cells by the calcium chloride method, and were transformed with pCDF-nprV plasmid constructed in (2) above. After selection using both Amp and streptomycin (Sm), a colony which grew was used in an expression experiment. A colony was chosen at random, and the cells were shake cultured (220 rpm) at 30° C. for 16 hours in LB medium containing 100 µg/mL Amp and 40 µg/mL Sm. After 20-fold dilution with LB medium, shake culture (220 rpm) was continued for further 3 hours at 30° C. IPTG then was added to the final concentration of 1 mM, and shake culture was continued for further 16-20 hours at 25° C. (220 rpm). The culture mixture was centrifuged at 3000 rpm for 30 minutes, and the supernatant was subjected to the measurement of AP enzyme activity and protease activity.

(4) Measurement of Protease Activity

To 150 µL of the substrate solution (50 mM Tris-HCl containing 0.1% azocasein, pH 7.4) was added 10 µL of a sample, and reaction was allowed for 10 minutes at 37° C. To this was added 150 µL of a stop solution (10% TCA) and the mixture was let stand for 10 minutes on ice. After centrifugation at 12000 rpm, at 4° C. for 4 minutes, the supernatant was transferred to a 96-well plate and read for $OD_{420}$ on a plate reader.

TABLE 3

Aminopeptidase activity

|  | AP | AP + nprV |
|---|---|---|
|  |  | (Unit: mU/mL) |
| Culture supernatant | 76.2 | 403.3 |
| Cell lysate | 361 | 21.5 |

TABLE 4

Protease activity

|  | AP | AP + nprV |
|---|---|---|
|  |  | $(OD_{420})$ |
| Culture supernatant | 0.009 | 0.126 |
| Cell lysate | −0.001 | 0.001 |

Figure 7:
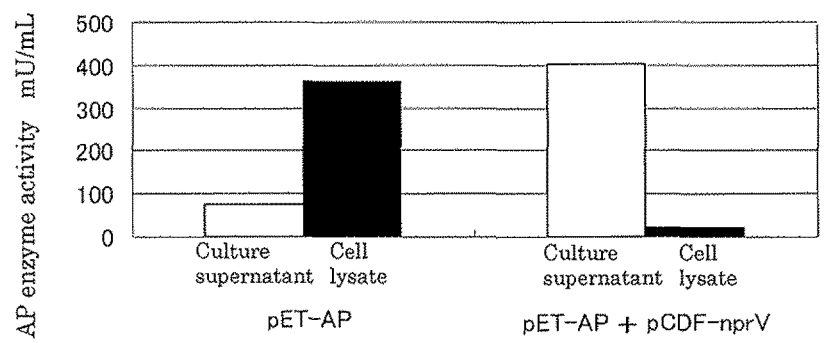
FIG. 7 is a graph showing the aminopeptidase activity in the culture supernatant and in the cell lysate, respectively, after expression of BL21(DE3)/pET-AP and BL21(DE3)/pET-AP&pCDF-riprV was induced with 1 mM IPTG at 25° C.

As seen in Table 3, 5-6 times greater AP activity was obtained in the culture supernatant in the case where both AP and nprV were introduced into the *E. coli*, than in the case where AP alone was introduced. This is about 15-20 times the AP activity produced by *V. proteolyticus*. Again, as seen in Table 4, with the *E. coli* cells in which both AP and nprV were co-expressed, high protease activity was observed in the supernatant. What is interesting is that AP activity was hardly detected in the cell extract from the *E. coli* in which both AP and nprV were co-expressed (FIG. 7). This suggests that co-expression of AP and nprV increases not only the conversion of AP in the culture supernatant to its active form but also the efficiency of AP secretion into the culture medium.

Example 2

Co-Expression of Mutant-Type Neutral Protease and Aminopeptidase (1) Preparation of Mutant-Type Neutral Protease Mutation was randomly introduced into nprV to obtain a mutant-type nprV which can be steadily expressed in *E. coli* as in an active form (named nprV-R). That is, an XL1-Red mutant strain (Stratagene, Cat #200129) in which mutation can be induced in vivo was used for performing random introduction of mutation. The XL1-Red mutant strain was transformed with pCDF-nprV, which was the nprV expression vector prepared above, and with thus obtained transformant, the agar+40 µg/mL Sm plates were inoculated. After a 24-hr culture at 37° C., 300 colonies were picked up and planted in 10 mL of LB+40 µg/mL Sm, and following an 18-hour culture at 37° C., plasmids were purified by the alkali-SDS method. BL21(DE3) cells were transformed with these plasmids, and LB agar+1.5% skimmed milk+40 µg/mL Sm+1 mM IPTG plates were inoculated with the cells (15 mm plate×2). After a 16-hour culture at 37° C., about 4000 colonies/plate were obtained. Out of the two plates (8000 colonies), one colony alone decomposed skim milk, forming a halo observed around it. This colony was suspended in 1.5 mL of LB+40 µg/mL Sm, and after an overnight culture at 37° C., was purified using GenElute Plasmid Miniprep Kit (Sigma, #PLN350). The nucleotide sequence of thus obtained nprV-R was confirmed. This nprV-R was found to have mutations at two positions. They were (1) a mutation at the 11th amino acid Trp (when counted including Ala inserted immediately after the first Met) to stop codon (Opal: TGA) in the amino acid sequence, which was due to a mutation of G to A at the nucleotide 33 (when counted including the GCA inserted immediately after the start codon) within the nucleotide sequence of the signal region, and (2) a mutation at the 183rd amino acid Ala (when counted including Ala inserted immediately after the first Met) to Val in the amino acid sequence of the preproprotein, which was due to a mutation of C to T at the nucleotide 548 (when counted including the OCA inserted immediately after the start codon) within the nucleotide sequence of the N-terminal propeptide region.

(2) Co-Expression of Mutant-Type Neutral Protease and Aminopeptidase

Figure 8:
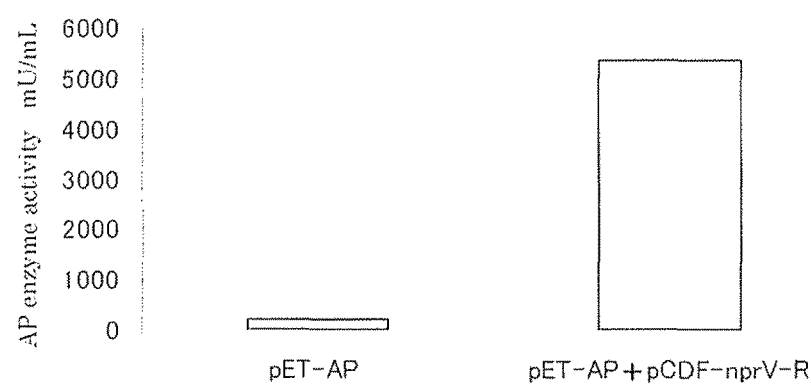
FIG. 8 is a graph showing the aminopeptidase activity in the culture supernatant after expression of BL21(DE3)/pET-AP and BL21 (DE3)/pET-AP&pCDF-nprV-R was induced with 1 mM IPTG at 25° C.

Then, in order to achieve co-expression of AP and nprV-R, BL21(DE3)/pCDF-nprV-R was transformed with pET-AP to generate BL21(DE3)/pCDF-nprV-R & pET-AP. A clone chosen at random was suspended in 1 mL of LB+100 µg/mL Amp+40 µg/mL Sm, cultured for 5 hours at 30° C., and then after addition of IPTG to the final concentration of 1 mM, culture was continued for further 17 hours at 30° C. Supernatant was obtained by centrifugation at 3000 rpm for 30 minutes. The AP activity in the supernatant was measured. As a result, not less than 20 times higher AP activity was observed with the E. coli in which the mutant neutral protease gene and the AP gene was co-expressed than in the control (BL21(DE3)/pET-AP) in which AP gene alone had been introduced (FIG. 8). This indicates that co-expression of the mutant-type neutral protease and aminopeptidase allows production of active aminopeptidase in the medium very efficiently.

The mutation (1) induced in the above neutral protease was found within the signal sequence, and the latter within the N-terminal propeptide sequence, respectively. If the codon created by the former mutation had been recognized as a stop codon, translation should have terminated there. However, as nprV activity was actually observed as shown in the above result, this codon is thought to have been read through and is very likely to have been translated as selenocysteine. It has been confirmed that the same result is obtained with a mutant-type gene in which the mutation within the signal sequence alone is reversed to normal (data not shown). Therefore, the mutation within the signal sequence is not essential.

Further, the mutation (2) is a mutation within the N-terminal propeptide (amino acids 26-197 in this mutant-type nprV-R in which a single amino acid has been inserted immediately after the N-terminal methionine: the nucleotide sequence of the mutant-type N-terminal propeptide is shown as SEQ ID NO:15, and the corresponding amino acid sequence as SEQ ID NO:16, respectively) (the mutation of C to T at the 473rd nucleotide in SEQ ID NO:15, and the resulting mutation of Ala to Val at the 158th amino acid in SEQ ID NO:16). Thus, this mutation does not affect the nucleotide or amino acid sequence of mature nprV (amino acids 197-609 in SEQ ID NO:12, the nucleotide sequence for the mature nprV is shown as SEQ ID NO:17, and the corresponding amino acid sequence as SEQ ID NO:18, respectively). It is thought that while natural-type N-terminal propeptide acts to inhibit the vibriolysin activity, this was prevented by introduction of the amino acid mutation (2) and thereby contributed to a steady expression of the activity.

INDUSTRIAL APPLICABILITY

The present invention greatly increases the efficiency of production of aminopeptidase. Therefore, the present invention is useful as a method for production of aminopeptidase which is used to selectively remove extra amino acids in the case where they are attached at the N-terminus of the proteins produced by microorganisms in the production of medicines and food stuff, in particular proteins in which the second amino acid residue from their N-terminus is proline, such as human growth hormone, C4-CSF, IL-2, and the like.

SEQUENCE LISTING

GP 1.16-PCT.ST25

---

We claim:

1. A method for production of an aminopeptidase comprising
   (a) transforming host *Escherichia coli* (*E. coli*) with an aminopeptidase gene and a vibriolysin gene,
   (b) culturing in a medium the host *E. coli* transformed in (a) to allow expression of both the aminopeptidase gene and the vibriolysin gene, and
   (c) collecting the aminopeptidase thus produced and released by the host *E. coli* into the culture supernatant, wherein the aminopeptidase, in the form of the preprotein thereof, has the amino acid sequence of SEQ ID NO: 4 and wherein the vibriolysin, in the form of the mature protein thereof, has the amino acid sequence of SEQ ID NO: 18.

2. The method of claim 1, wherein the aminopeptidase gene and the vibriolysin gene both originate from *Vibrio proteolyticus* (*V. proteolyticus*).

3. The method of claim 1, wherein the aminopeptidase gene is a gene for an aminopeptidase wherein the peptide bond-cleaving reaction catalyzed by the aminopeptidase stops one residue before a proline residue.

4. The method of claim 1, wherein the vibriolysin gene comprises a mutation which results in a mutation of an amino acid residue within the N-terminal propeptide region of the protein encoded by said vibriolysin gene.

5. The method of claim 1, wherein the vibriolysin gene comprises mutation which results in a mutation of Ala to Val occurring at the 158th amino acid residue within the N-terminal propeptide region of the protein encoded by said vibriolysin gene.

6. The method of claim 1, wherein the vibriolysin gene comprises a mutation which results in a mutation of Ala to Val occurring at the 158th amino acid residue within the N-terminal propeptide region of the protein encoded by the vibriolysin gene, and wherein the vibriolysin gene comprises the nucleic acid sequence of SEQ ID NO: 15.

7. The method of claim 1, comprising transforming the host *E. coli* with a *V. proteolyticus* vibriolysin gene and a *V. proteolyticus* aminopeptidase gene.

8. A method for production of an aminopeptidase comprising
   (a) culturing a host *E. coli* transformed with an aminopeptidase gene and with a vibriolysin gene in a medium whereby both genes are expressed; and (b) collecting the thus-expressed aminopeptidase produced and released by the host *E. coli* into the culture medium, wherein the aminopeptidase, in the form of the preproprotein thereof, has the amino acid sequence of SEQ ID NO: 4 and wherein the vibriolysin, in the form of the mature protein thereof, has the amino acid sequence of SEQ ID NO: 18.

* * * * *